US00PP10267P

United States Patent [19]

Enthoven

[11] Patent Number: Plant 10,267

[45] Date of Patent: Mar. 3, 1998

[54] GERANIUM PLANT NAMED 'MERIFLAME'

[75] Inventor: Adrianus W. M. Enthoven, Wateringen, Netherlands

[73] Assignee: Enthoven Breeding B.V., Wateringen, Netherlands

[21] Appl. No.: 762,702

[22] Filed: Dec. 9, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—C. A. Whealy

[57] ABSTRACT

A new and distinct cultivar of geranium plant named 'Meriflame', characterized by its compact, rounded and upright growth habit; moderate growth rate and vigor; fast rooting; medium green foliage color with distinct zonation; large umbels with about 25 flowers per umbel; semi-double dark orange red flowers that do not burn under high light; and good weather and stress tolerance.

2 Drawing Sheets

The present invention relates to a new and distinct cultivar of geranium plant, botanically known as *Pelargonium* × *hortorum*, and hereinafter referred to by the cultivar name Meriflame.

The new cultivar is a product of a planned breeding program conducted by the inventor in Wateringen, The Netherlands. The objective of the breeding program was to develop new zonal geranium cultivars with semi-double flowers, fast rooting, tolerane to Botrytis, weather resistance, compact plant growth habit, and interesting and unique flower colors.

The new cultivar originated from a cross made by the inventor of the proprietary seedling selection A234 as the male, or pollen, parent with the proprietary seedling selection A111 as the female, or seed, parent. The cultivar 'Meriflame' was discovered and selected by the inventor as a flowering plant within the progeny of the stated cross in a controlled environment in Wateringen, The Netherlands, In June, 1990.

Compared to plants of the male parent, plants of the new cultivar have darker green leaves. Plants of the new cltivar have semi-double flowers whereas plants of the female parent have single flowers.

Asexual reproduction of the new cultivar by terminal cuttings taken at Wateringen, The Netherlands, has shown that the unique features of this new geranium are stable and reproduced true to type in successive generations of asexual reproduction.

The following traits have been repeatedly observed and are determined to be the unique characteristics of 'Meriflame'. These characteristics in combination distinguish 'Meriflame' as a new and distinct cultivar:

1. Compact, rounded and upright growth habit.
2. Moderate growth rate and vigor.
3. Fast rooting.
4. Medim green foliage color with distinct zonation.
5. Large umbels with about 25 flowers per umbel.
6. Semi-double dark orange red flowers that do not burn under high light.
7. Good weather and stress tolerance.

The new geranium can be compared to the cultivar 'Fisboogy' (U.S plant patent applied for). Plants of the new cultivar differ from plants of the cultivar 'Fisboogy' in the following characteristics:

1. Plants of the new cultivar are more compact than plants of the cultivar Fisboogy.
2. The zone on foliage of plants of the new cultivar is more distinct than the zone on foliage of plants of the cultivar 'Fisboogy'.

3. Plants of the new cultivar have a more intense flower color than plants of the cultivar 'Fisboogy'.
4. Flowers of the new cultivar have thicker petals that do not burn under high light compared to flowers of the cultivar 'Fisboogy'.

The new geranium can also be compared to the cultivar 'Meriking' (disclosed in U.S. Plant Pat. No. 9,156). Plants of the new cultivar differ from plants of the cultivar Meriking in the following characteristics:

1. The zone on foliage of plants of the new cultivar is more distinct than the zone on foliage of plants of the cultivar 'Meriking'.
2. Plants of the new cultivar have broader petals than plants of the cultivar 'Meriking'.
3. Flowers of the new cultivar have markings on its upper petals whereas plants of the cultivar 'Meriking' are devoid of markings on the flower petals.

The accompaning colored photographs illustrate the overall appearance of the new cultivar, showing the colors as true as it is reasonably possible to obtain in colored reproductions of this type.

The first photograph comprises a top perspective view of a typical potted plant of 'Meriflame'.

The second photograph comprises a close-up view of a typical flower of 'Meriflame'.

The third photograph comprises a close-up view of typical leaves of 'Meriflame'.

Foliage and flower colors in the photograph may appear different from the actual colors due to light reflectance.

The cultivar 'Meriflame' has not been observed under all possible environmental conditions. The phenotype may vary somewhat with variations in environment such as temperature and light intensity, without, however, any variance in genotype. The following observations, measurements and comparisions describe plants grown in Wateringen, The Netherlands, under commercial practice in a glass-covered greenhouse with day temperatures of 20C and night temperatures of 18C and light levels of 450 W/m$^2$.

In the following description, color references are made to The Royal Horticultural Society Colour Chart Execept where general terms of ordinary dictionary significance are used.

Classification:

*Botanical.*—*Pelargonium*×*hortorum* cv. 'Meriflame'.

*Commercial.*—Zonal geranium.

Parentage:

*Male parent.*—Proprietary seedling selection A234.

*Female parent.*—Proprietary seedling selection A111.

Propagation:

*Type cutting.*—Terminal cuttings.

*Time to initiate and develop roots.*—Summer: About 16 days at 20C. Winter: 16 to 20 days at 20C.

*Rooting habit.*—Vigorous, fast to root, freely branching.

Plant description:

*General appearance.*—Rounded and upright growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—Soil level to top of leaves: About 15 cm. Soil level to top of flowers: About 25 cm.

*Branching habit.*—Moderate to low branching with about 3 lateral branches per plant.

*Internode length.*—About 2 cm.

*Foliage description.*—Arrangement: Alternate. Shape: Generally reniform with cordate base. Aspect: Slightly undulating. Size: Length: 4.5 to 6 cm. Width: 8 to 10 cm. Texture: Velvety, pubescent on abaxial and adaxial surfaces. Margin: Crenate. Zonation: Distinct zone, 1.2 to 2 cm in width and 1 to 1.5 cm from margin. Color: Abaxial surface: 137B. Adaxial surface: 137C. Zonation, abaxial surface only: 137A/141A. Venation pattern: Palmate. Petiole: Length: 6 to 8 cm. Diameter: 3 to 4 mm. Color: 137C. Durability to rain, wind and stress conditions: Very good.

Flowering description:

*Flowering habit.*—Semi-double flowers arranged in umbels.

*Natural flowering season.*—Spring throughout summer.

*Flower longevity.*—Flowers last about 2.5 weeks on the plant.

*Flowers borne.*—Flower buds develop in apical leaf axils. Umbels are displayed above the foliage.

*Umbels.*—Form: Rounded. Quantity of flowers per umbel: About 25. Diameter: 9 to 10 cm. Depth (height): About 6 cm.

*Flowers: Form: Semi-double. Shape: Rounded. Diameter:* 4 to 4.5 cm. Depth (height): 1.5 to 2.5 cm. Quantity of petals and petaloids per flower: About 10.

*Petals.*—Shape: Obovate with rounded apex. Arrangement: Rosette, overlapping. Aspect: Flat. Size: Length: 2.2 to 2.5 cm. Width: 1.9 to 2.3 cm. Texture: Satiny, smooth. Margin: Entire. Color: Opened flower, upper petals, adaxial surface: 40A. Opened flower, upper petals, abaxial surface: 41A. Opened flower, lower petals, adaxial surface: 40A. Opened flower, lower petals, abaxial surface: 40B.

*Petaloids.*—Shape: Irregular, generally obovate with rounded apex. Arrangement: Rosette, overlapping. Size: Length: 1.5 to 2.5 cm. Width: About 1.5 cm. Texture: Satiny, smooth. Margin: Entire: Color: 40A.

*Peduncle (umbel stem).*—Angle: Erect. Size: Length: 10 to 12 cm. Diameter: About 5 mm. Texture: Pubescent. Color: Medium green with reddish tones.

*Pedicel (individual flower stem).*—Angle: Between 45° to 90° from vertical. Size: Length: 2.5 to 2.8 cm. Diameter: 1 to 2 mm. Texture: Pubescent. Color: Dark reddish green.

*Flower bud.*—Shape: Spherical. Size: Length: About 5 mm. Diameter: About 5 mm. Color: Light green with red tones at base.

*Sepals.*—Shape: Narrowly lanceolate with acuminate apex. Arrangement: Rosette. Quantity: 5. Size: Length: About 1.2 cm. Width: About 3 mm. Texutre: Smooth. Margin: Entire. Color: Light green with reddish base.

*Reproductive organs.*—Androecium: Stamen number: 5 to 10. Anther shape: Elongated oval. Anther size: About 2 mm. Pollen color: 42B. Gynoecium: Pistil number: 1. Pistil length: About 8 mm. Stigma shape: Decurrent. Stigma color: 54A. Style length: About 3 mm. Style color: 54A.

Disease resistance: No fungal, bacterial nor viral problems observed under commercial conditions.

Seed development: Seed production is very rarely observed.

It is claimed:

1. A new and distinct cultivar of geranium plant named 'Meriflame', as illustrated and described.

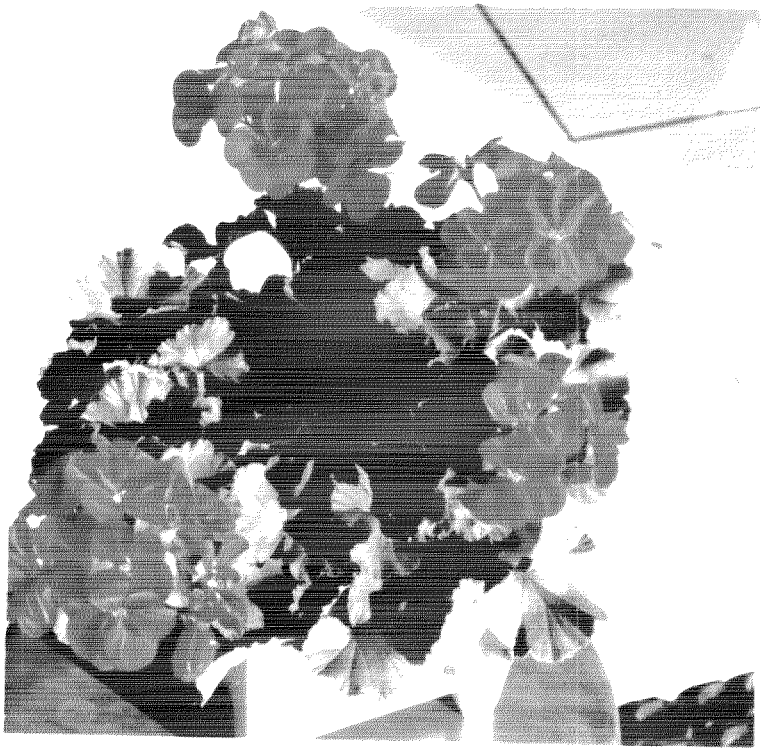

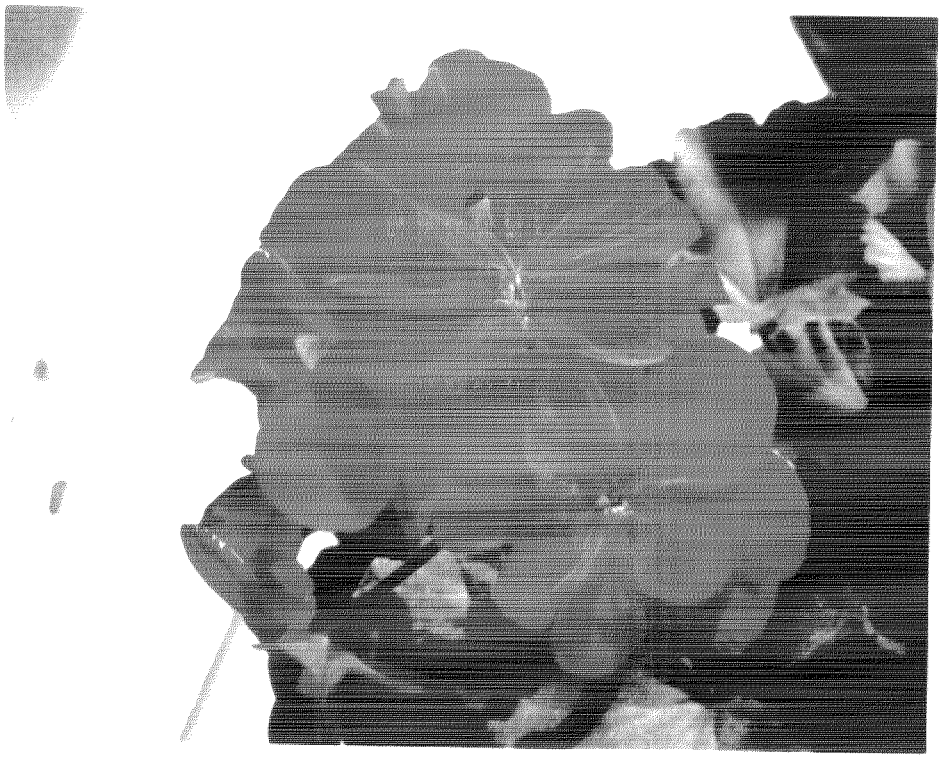
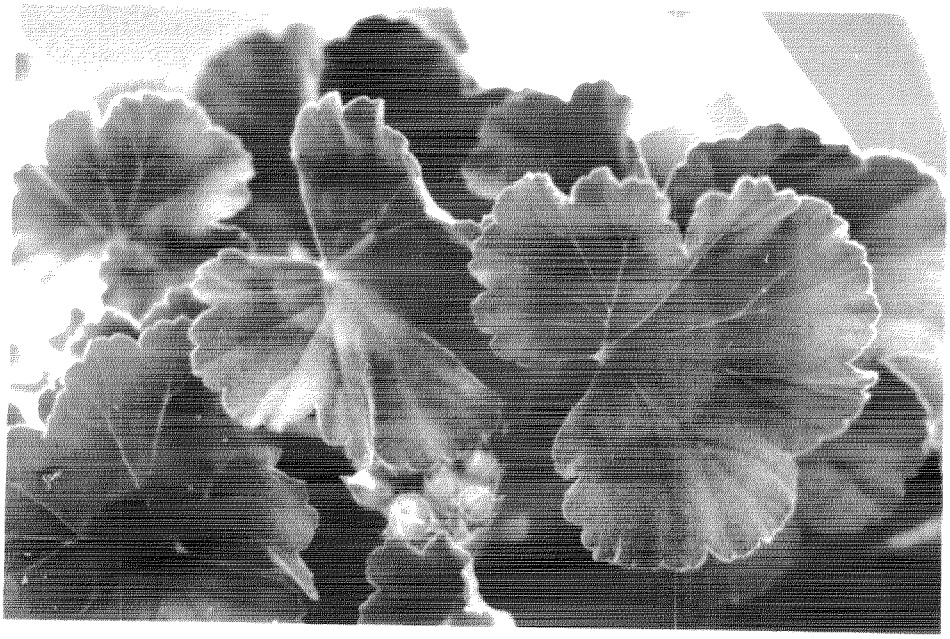

* * * * *